(12) United States Patent
Hauck

(10) Patent No.: US 8,644,950 B2
(45) Date of Patent: *Feb. 4, 2014

(54) CARDIAC TISSUE ELASTICITY SENSING

(75) Inventor: John A. Hauck, Shoreview, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 90 days.

This patent is subject to a terminal disclaimer.

(21) Appl. No.: 13/413,235

(22) Filed: Mar. 6, 2012

(65) Prior Publication Data

US 2012/0165702 A1  Jun. 28, 2012

Related U.S. Application Data

(62) Division of application No. 11/845,250, filed on Aug. 27, 2007, now Pat. No. 8,131,379.

(51) Int. Cl.
  *A61N 1/08* (2006.01)
  *A61B 5/02* (2006.01)

(52) U.S. Cl.
  USPC ............ 607/99; 600/508; 600/547; 600/587; 607/96; 607/101; 607/113

(58) Field of Classification Search
  None
  See application file for complete search history.

(56) References Cited

U.S. PATENT DOCUMENTS

| | | | |
|---|---|---|---|
| 3,249,103 A | 5/1966 | Woodhouse | |
| 5,396,887 A | 3/1995 | Imran | |
| 5,588,432 A | 12/1996 | Crowley et al. | |
| 5,766,137 A * | 6/1998 | Omata | 600/587 |
| 5,911,694 A * | 6/1999 | Ikeda et al. | 600/587 |
| 6,231,520 B1 * | 5/2001 | Maezawa | 600/552 |
| 8,131,379 B2 * | 3/2012 | Hauck | 607/101 |
| 2004/0102722 A1 | 5/2004 | Naghavi | |
| 2004/0210136 A1 | 10/2004 | Varghese et al. | |
| 2005/0033199 A1 | 2/2005 | Van der Steen et al. | |
| 2006/0184025 A1 | 8/2006 | Sumi | |

* cited by examiner

*Primary Examiner* — Kennedy Schaetzle
(74) *Attorney, Agent, or Firm* — Marsh Fischmann & Breyfogle LLC

(57) ABSTRACT

A system and method are provided for assessing the compliance of internal patient tissue for purposes of catheter guidance and/or ablation procedures. Specifically, the system/method provides for probing internal patient tissue in order to obtain force and/or tissue displacement measurements. These measurements are utilized to generate an indication of tissue elasticity. In one exemplary embodiment, the indication of elasticity is correlated with an image of the internal tissue area and an output of this image including elasticity indications is displayed for a user.

25 Claims, 8 Drawing Sheets

CARDIAC TISSUE ELASTICITY SENSING

CROSS REFERENCE TO RELATED APPLICATION

This application is a divisional application of U.S. patent application Ser. No. 11/845,250 entitled "Cardiac Tissue Elasticity Sensing" having a filing date of Aug. 27, 2007 and which issued as U.S. Pat. No. 8,131,379 on Mar. 6, 2012, the entire contents of which is incorporated herein by reference.

BACKGROUND OF THE INVENTION a. Field of the Invention

The instant invention is directed toward an electrode catheter and a method for using the electrode catheter for tissue mapping, guidance and/or tissue ablation. In particular, the electrode catheter of the present invention may assess tissue elasticity in-vivo to facilitate catheter guidance and/or ablation.

b. Background Art

Catheters have been in use for medical procedures for many years. Catheters can be used for medical procedures to examine, diagnose, and treat while positioned at a specific location within the body that is otherwise inaccessible without more invasive procedures. During these procedures a catheter is typically inserted into a vessel near the surface of the body and is guided to a specific location within the body for examination, diagnosis, and treatment. For example, catheters can be used to convey an electrical stimulus to a selected location within the human body, e.g., for tissue ablation. Catheters with sensing electrodes can be used to monitor various forms of electrical activity in the human body, e.g., for electrical mapping.

Catheters are used increasingly for medical procedures involving the human heart. Typically, the catheter is inserted in an artery or vein in the leg, neck, or arm of the patient and threaded, sometimes with the aid of a guide wire or introducer, through the vessels until a distal tip of the catheter reaches the desired location for the medical procedure in the heart. In the normal heart, contraction and relaxation of the heart muscle (myocardium) takes place in an organized fashion as electro-chemical signals pass sequentially through the myocardium.

Sometimes abnormal rhythms occur in the heart, which are referred to generally as arrhythmia. The cause of such arrhythmia is generally believed to be the existence of an anomalous conduction pathway or pathways that bypass the normal conduction system. These pathways can be located in the fibrous tissue that connects the atrium and the ventricle.

An increasingly common medical procedure for the treatment of certain types of cardiac arrhythmia is catheter ablation. During conventional catheter ablation procedures, an energy source is placed in contact with cardiac tissue (e.g., associated with a anomalous conduction pathway) to create a permanent scar or lesion that is electrically inactive or non-contractile. The lesion partially or completely blocks the stray electrical signals to lessen or eliminate arrhythmia.

Ablation of a specific location within the heart requires the precise placement of the ablation catheter within the heart. Precise positioning of the ablation catheter is especially difficult because of the physiology of the heart, particularly because the heart continues to beat throughout the ablation procedures. Commonly, the choice of placement of the catheter is determined by a combination of electrophysiological guidance and computer generated maps/models that may be generated during a mapping procedure. Accordingly, it is desirable that any map or model of the heart be as accurate as practicable.

Several difficulties may be encountered, however, when attempting to form lesions at specific locations. One such difficulty is obtaining access to specific areas of the heart. For instance, access to the left atrium and pulmonary veins often requires performing a transseptal procedure where a catheter or other instrument is pushed through the interatrial septum between the left and right atriums. Such an instrument preferably punctures the septum at its thinnest location, for example the fossa ovalis. This location is not readily determined using conventional imaging techniques such as fluoroscopy or intracardial mapping. Instead, the physician determines the puncture location based on his/her experience using the electrode catheter to probe the interatrial septum to identify the most compliant location, typically the fossa ovalis. Such experience only comes with time, and may be quickly lost if the physician does not perform the procedure on a regular basis.

Another difficulty is selecting the proper amount of ablation energy to form a lesion. In this regard, the energy required to form a lesion of a desired dimension relates to several factors, including the force applied by the electrode to the tissue. Such force is dependent upon the compliance of the tissue, which may be a function of the thickness of the tissue. However, tissue compliance is not readily determined using conventional imaging techniques.

BRIEF SUMMARY OF THE INVENTION

It is often desirable to be able to assess the compliance of internal patient tissue for purposes of catheter guidance and/or ablation procedures. Accordingly, it has been determined that the compliance or 'elasticity' may be determined by probing internal tissue and measuring the resistive force of the tissue and/or the displacement of the tissue.

According to one aspect, a system and method for performing a medical procedure is provided. The system/method includes positioning a catheter at a first position relative to a first tissue location of an internal tissue area. A first force measurement is then obtained as indicative of a first force between the catheter and the first tissue location. This first force measurement may then be utilized to generate a tissue elasticity value that is associated with the first tissue location. Once such an elasticity value is determined, a medical procedure may be performed based at least in part on this information.

Such medical procedures include, without limitation, utilizing one or more tissue elasticity values to determine a location to puncture an internal tissue area. For instance, a region of the tissue area having the lowest elasticity value may correspond with the thinnest section of the tissue area. For instance, this area may correspond to the fossa ovalis. Accordingly, a catheter or another device may puncture this location in a transseptal procedure. In another arrangement, the elasticity values for the tissue area may be utilized to select ablation powers and/or contact forces for use during ablation procedures.

Positioning the catheter relative to the internal tissue area may include identifying an initial contact position where the catheter initially contacts the tissue at the first location. Positioning may further entail displacing the electrode catheter a first distance relative to the initial contact location, for example, to the first position. The electrode catheter may be displaced a second distance relative to the initial contact location to a second position to obtain a second force measurement. In one arrangement, the first and second force measurements, as well as the first and second displacement values, may be utilized to generate the elasticity value. In further arrangements, additional displacements and force measurements may be obtained.

In one arrangement, a robotic actuator may be utilized to displace the catheter relative to the initial contact location. In such an arrangement, the robotic actuator may provide controlled displacement and/or output displacement values for use in determining elasticity. In another arrangement, a catheter displacement sensor may be utilized to measure catheter displacement.

The system/method may further entail positioning the catheter at a plurality of tissue locations and generating a tissue elasticity value for each location. In this regard, the elasticity of the internal tissue area may be mapped. Such mapping may allow for the identification of structures of interest such as the fossa ovalis and/or previous ablation areas within the internal tissue area. That is, differences in elasticity may be used for the identification of structures of interest.

In one arrangement, stored data indicative of predetermined elasticity values may be utilized to generate an elasticity value for the force. That is, the force measurement may be utilized with, for example, predetermined look-up tables, equations, or other data (e.g., collectively catalog data) to determine an elasticity value for a tissue location. In another arrangement, the force measurement may be compared data values in put by an operator. That is, the measured force value may be compared to values set by an operator based on the experience of the operator.

The system/method may further entail generating a display output of the internal tissue area. Such a display output may provide a visual indication of the differing elasticity values for different location regions of the internal tissue area. For instance, modeling of the different elasticity values may be performed in order to generate a surface model based on the elasticity of the tissue area. Further, areas of different elasticity may have different visual indications (e.g., colors) to allow a user to visually identify areas of interest. Accordingly, such an output may be utilized for catheter guidance, ablation procedures and/or other procedures.

Determining force may include measuring an output of a transducer that is connected to a contact surface of the catheter. Determining force may further entail obtaining force and direction information. That is, the directional information may be indicative of a contact angle between the contact surface of the catheter and the tissue. Such force and direction measurements may be obtained utilizing a three-axis transducer. However, it will be appreciated that single-axis transducers may be utilized as well. In further arrangements, force measurements may be equated to impedance measurements. In such a system, the catheter may include one or more electrodes that contacts the tissue. Accordingly, by measuring the impedance an indication of the force of the contact the electrode and tissue may be generated.

According to another aspect, a system/method for performing a medical procedure is provided. The system/method includes providing an imaging system for generating an image of an internal tissue area of interest. The system/method further entails probing the internal tissue area to obtain an indication of tissue elasticity for at least a first location within the tissue area. Based on the indication of tissue elasticity, the image of the internal tissue area may be altered to provide a visual indication of the tissue elasticity at the first location. That is, tissue elasticity values may be correlated with an image of an internal tissue area.

Probing may entail contacting the internal tissue area utilizing a catheter. Accordingly, the catheter may be displaced against the tissue at the first location to obtain a first force measurement and may be advanced relative to the first position to obtain a second force measurement. Accordingly, these first and second force measurements and displacements associated with the first and second tissue displacements may be utilized to generate the indication of tissue elasticity.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 1a is a detailed illustration of the patient's heart in FIG. 1, showing the electrode catheter after it has been moved into the patient's heart.

DETAILED DESCRIPTION OF THE INVENTION

Exemplary embodiments of a catheter system and methods of using the system to measure tissue elasticity are depicted in the figures. As described further below, measuring tissue elasticity, as provided by the present invention, provides a number of advantages including, for example, the ability to locate a structure(s) of interest based on the elasticity of the structure and/or the elasticity of surrounding structure. Measuring tissue elasticity also allows for determining force applied to tissue, which may allow enhanced control of lesion dimensions.

Figure 1:
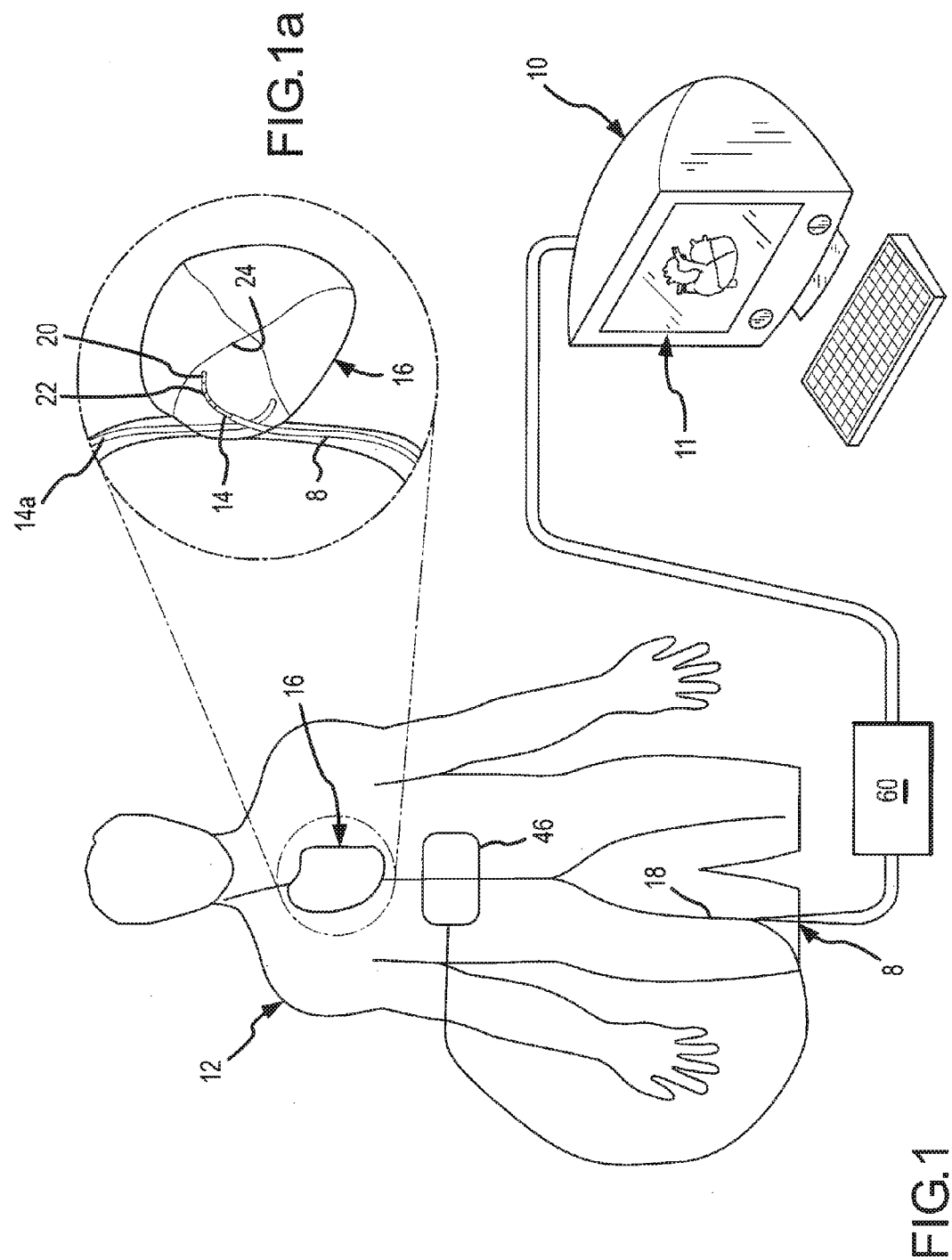
FIG. 1 is a diagrammatic illustration of an exemplary catheter system, which may be implemented to access internal patient tissue for mapping and/or tissue ablation procedures.

FIG. 1 is a diagrammatic illustration of an exemplary electrode catheter system 10 which may be implemented to access and map internal patient tissue and/or perform medical procedures on such tissue. Further, the system 10 is operative to assess tissue elasticity to assist in tissue mapping, catheter guidance, ablation procedures and/or other procedures. The catheter system 10 may include a guiding introducer having a sheath 8, which may be inserted into the patient 12. The sheath 8 may provide a lumen for the introduction of a catheter 14 which may be disposed beyond the distal insertion end of the sheath 8. During an exemplary procedure, a user (e.g., the patient's physician or a technician) inserts the sheath of a guiding introducer into one of the patient's blood vessels 18, e.g., through the leg (as shown in FIG. 1) or the patient's neck. The user, guided by an imaging device (e.g., fluoroscopy, ICE, electro-anatomical mapping, etc.) moves the sheath 8 into the patient's heart 16 (as shown in more detail in FIG. 1a).

When the sheath 8 of the guiding introducer is positioned in a desired location within the heart 16 of the patient, the electrode catheter 14 may be extended through a lumen of the sheath 8 such that the electrode catheter 14 may be guided to a desired location within the heart to perform, for example tissue mapping and/or tissue ablation. In tissue mapping procedures, a model of the heart may be generated on an output display 11, which may be utilized for subsequent catheter guidance. One or more additional catheters 14a may also be utilized during mapping and/or subsequent procedures. In addition, a robotic actuator 60 may be utilized to partially or completely control catheter movement.

Figure 2:
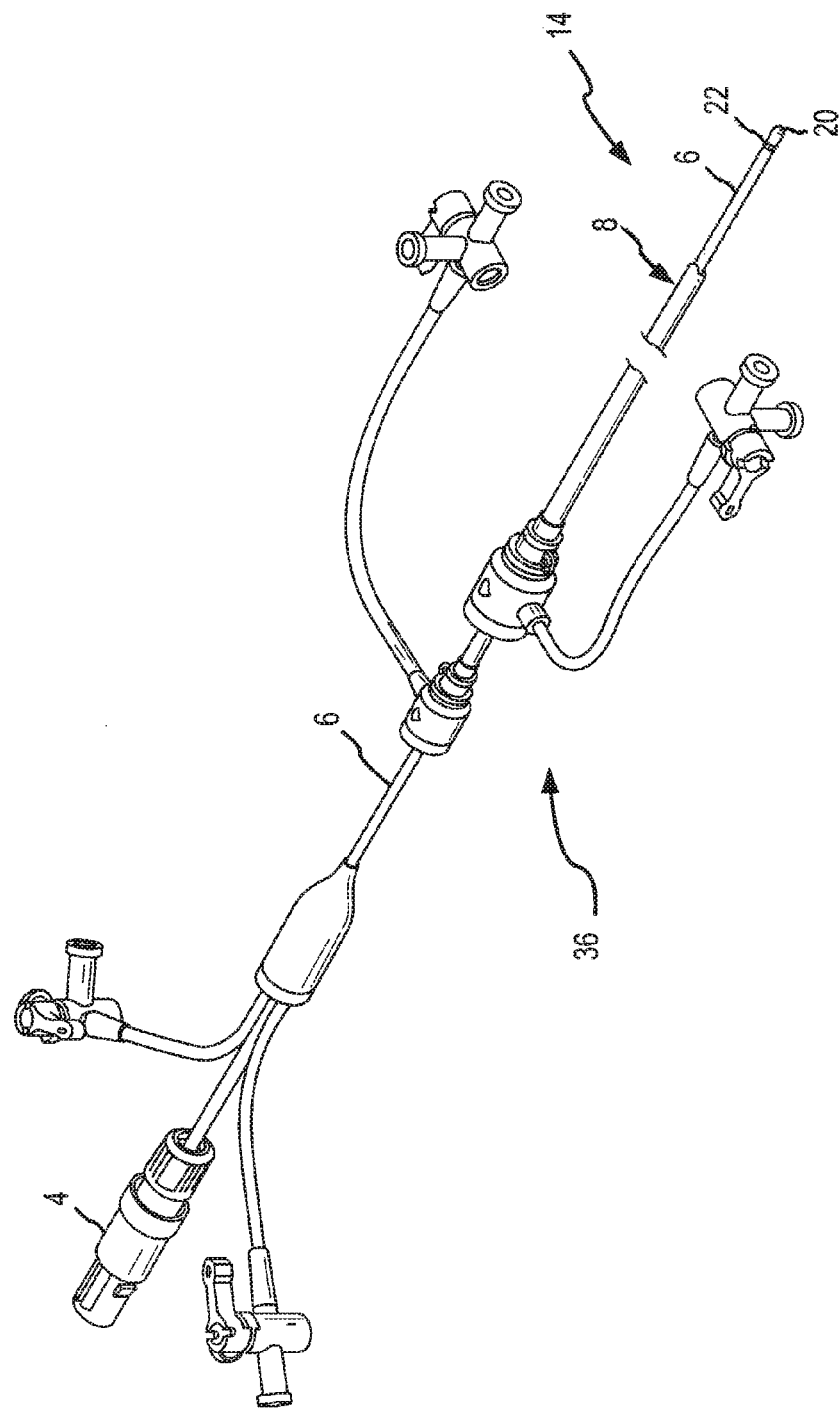
FIG. 2 is an exemplary introducer and catheter that may be utilized with the system of FIG. 1

FIG. 2 illustrates one embodiment of a guiding introducer system 36 with an electrode catheter 14 that may be selectively extended from the distal end portion of the sheath 8. As used herein and commonly used in the art, the term "distal" is used generally to refer to components of the catheter system, such as the tip electrode 20, located toward the insertion end of the of the ablation catheter 14 (i.e., toward the heart or other target tissue when the catheter is in use). In contrast, the term "proximal" is used generally to refer to components or portions of the catheter that are located or generally orientated toward the non-insertion end of the catheter (i.e., away from or opposite the heart or other target tissue when the catheter is in use).

The sheath 8 is a tubular structure defining at least one lumen or longitudinal channel. The sheath 8 is used to introduce and guide the catheter 14 to a targeted internal tissue area. The catheter 14, however, may be used alone or with other guiding and introducing type devices depending on the particular procedure being performed. As shown in FIG. 2, the catheter includes a tubular body or shaft 6 extending from a proximal handle 4, through the sheath 8 and extending out of the distal end of the sheath 8. The proximal handle 4 or a proximal portion of the shaft 6 may be connected to a robotic actuator. In one exemplary embodiment, the sheath 8 and shaft 6 are fabricated with a flexible resilient material. The sheath and the components of the catheter are preferably fabricated of materials suitable for use in humans, such as polymers. Suitable polymers include those well known in the art, such as polyurethanes, polyether-block amides, polyolefins, nylons, polytetrafluoroethylene, polyvinylidene fluoride, and fluorinated ethylene propylene polymers, and other materials. In the particular ablation system configuration of FIG. 2, the sheath 8 is configured to receive and guide the catheter 14 within an internal lumen to a location in the heart once the sheath is pre-positioned in an appropriate location.

The electrode catheter 14 of the exemplary embodiment includes a tip electrode 20 and a force transducer 22. The force transducer 22 is operative generate an output that is indicative of a force applied to the tip electrode 20 or to other elements attached to the end of the electrode catheter (e.g., needles, transducers, etc). Non-limiting examples of force transducers that may be utilized include pressure transducers and strain gages. Exemplary transducers that may be utilized are variously disclosed in U.S. patent application Ser. No. 11/647,314, filed 29 Dec. 2006 entitled "Pressure-sensitive conductive composite contact sensor and method for contact sensing"; U.S. patent application Ser. No. 11/647,316, filed 29 Dec. 2006 entitled "Pressure-sensitive conductive composite electrode and method for ablation"; U.S. patent application Ser. No. 11/647,279, filed 29 Dec. 2006 entitled "Design of ablation electrode with tactile sensor"; U.S. patent application Ser. No. 11/647,294, filed 29 Dec. 2006 entitled "Contact-sensitive pressure-sensitive conductive composite electrode and method for ablation"; U.S. patent application Ser. No. 11/549,100, filed 12 Oct. 2006 entitled "Dynamic contact assessment for electrode catheters"; and U.S. patent application Ser. No. 11/553,965, filed 27 Oct. 2006 entitled "Systems and methods for electrode contact assessment", the entire contents of which are incorporated by reference herein.

In one exemplary embodiment, the force transducer is a three-axis transducer that is operative to generate vector information. In this regard, if the tip electrode 20 is contacted with a tissue wall, the force applied to the tip electrode 20 as well as the angle the tip electrode 20 contacts the wall may be determined. In another embodiment, the force transducer may be incorporated at the proximal end of the catheter. Further, in robotic systems, motor current representing applied motor torque may be calibrated to yield an applied force at the catheter tip. It will be appreciated other electrical parameters of the motor/robotic system may also be utilized to generate an indication of applied force.

The tip electrode 20 and/or electrodes of another catheter 14a may be implemented to electrically map the myocardium (i.e., muscular tissue in the heart wall). In this regard, information from the electrode(s) may be utilized to create realistic model of cardiac chamber geometries or models of other internal tissue depending on the particular procedure being performed. Such a model may be displayed on a user output 11 (See FIG. 1) for use in catheter navigation, for example, during an ablation procedure performed after mapping.

To create the model, any appropriate positioning/location system that allows for internal mapping and modeling can be used. One such exemplary positioning/location system is the NavX endocardial mapping system produced by St. Jude Medical Inc. In one embodiment, two or more external patient electrode patches 46 (only one shown) are applied on two or more locations on the body. An electrical signal is transmitted between the patches 46, and one or more electrodes of one or more catheters 14 within the heart sense the signal. The system 10 collects electrical data from the catheter(s) 14 and uses this information to track catheter movement and construct three-dimensional (3-D) models of the heart chamber in which the catheter is positioned. Additionally a physician may sweep the catheter(s) 14 across the heart chamber during data collection to outline the structures and relay the signals to the computer system, which generates the 3-D model. The resulting model may then be utilized to, for example, guide the catheter 14 to one or more locations in the heart where treatment is needed. During mapping, it may be desirable that one of the electrode catheters 14 and/or 14A include a plurality of electrodes for receiving electrical signals. Further, such electrodes may be disposed, for example, in a spiral pattern such that there is a three dimensional displacement of these receiving electrodes. In this arrangement, data gathered by the dispersed three-dimensional array of electrodes may allow for improved mapping of the interior of, for example, a cardiac chamber. Such a system allows for the creation of detailed internal models at the time of study and/or performance of an internal procedure. This is, the system may be operative to generate substantially real-time models.

During catheter ablation, a physician advances the catheter 14 to target tissue utilizing the model. An ablation electrode, for example, tip electrode 20, is then maneuvered to contact targeted tissue. Current is then applied to the catheter electrode 20. This current passes through the catheter electrode 20, through patient tissue and back to the external electrode patch 46 on the body surface of the patient. The myocardium around the catheter electrode 20 is heated by Joule effect. When the myocardial temperature exceeds a predetermined threshold (e.g., 50° Celsius) the tissue loses electrical excitability. Stated otherwise, application of electrical energy creates a lesion within the targeted tissue. Accordingly, accurate mapping of the tissue is necessary to properly locate target tissue and create lesions to prevent undesired electrical activity.

In addition to accuracy of mapping, success of the ablation procedure is dependent upon effective lesion formation. Generally, the size of a lesion is affected by a number of physiological and catheter dependent variables. For instance, catheter tissue contact, catheter geometry, blood flow around ablation site, applied power, duration, and temperature of the ablation electrode all affect lesion creation. Another variable that affects the creation of a lesion is the force applied by the electrode to the tissue. Applied force is related to the mechanical compliance or 'elasticity' of the tissue. Accordingly, knowledge of the elasticity of the tissue prior to lesion formation may permit correct application of force to the tissue during an ablation procedure. Further, the elasticity of the tissue may change over a tissue area of interest. Knowledge of changes in tissue elasticity may also allow for variable force application during lesion formation.

Figure 3A:
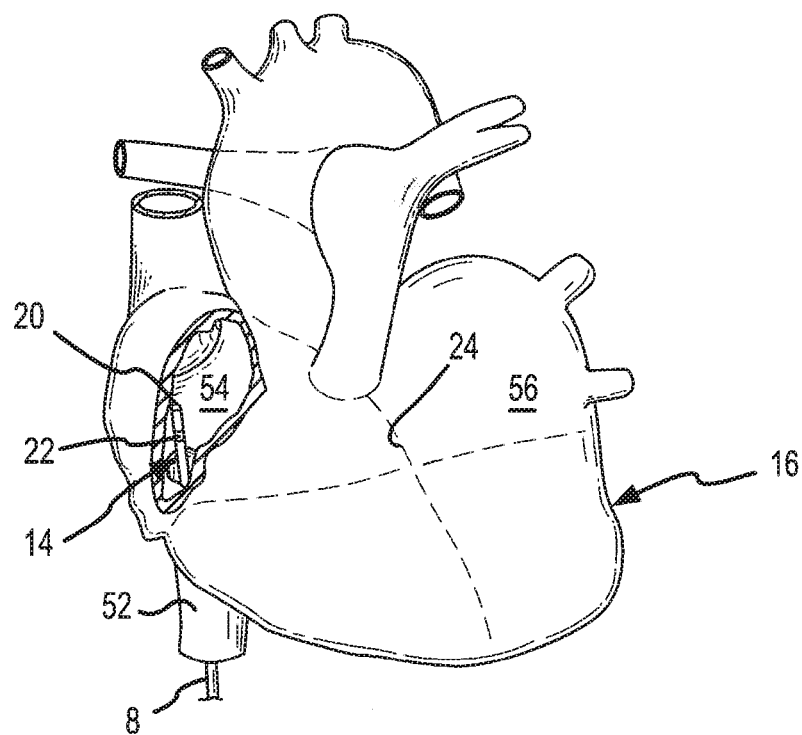
FIGS. 3A and 3B illustrate catheter placement within a patient's heart.

The knowledge of tissue elasticity may facilitate additional procedures as well. For instance, identification of the elasticity of the different areas within a heart chamber may allow for guiding a catheter to a desired location. In one exemplary arrangement, tissue elasticity may facilitate transseptal catheter guidance. As may be appreciated, cardiac access is often provided by inserting the sheath 8 in the femoral vein in the right leg. The sheath is then maneuvered up to the inferior vena cava 52 and into the right atrium 54. See FIG. 3A. In what is typically referred to as a transseptal approach, the sheath and/or a catheter extending through the sheath is passed through the interatrial septum 24 between the right atrium 54 and left atrium 56. This provides access to the left atrium 56 as well as the pulmonary veins.

Figure 3B:
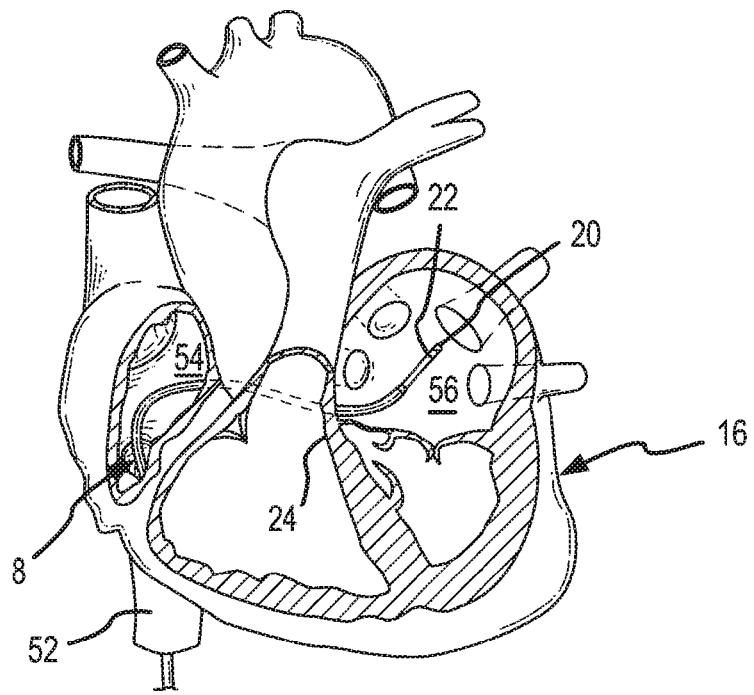

Such transseptal access may be achieved by positioning the sheath 8 at the appropriate location in the right atrium 54 and extending a dilator and a needle (not shown) through a lumen of the sheath 8. When the dilator and needle are within the sheath 8, the ablation catheter 14 may be removed from the sheath 8. In an exemplary transseptal procedure, the needle is pressed through the interatrial septum 24 between the right and left atriums. Following the needle, the dilator is pressed through the small opening made by the needle. The dilator expands the opening sufficiently so that the sheath 8 may then be pressed through the opening to gain access to the left atrium 56 and the pulmonary veins. With the sheath in position, the dilator is removed and the catheter 14 is extended into the lumen of the sheath 8 and pushed along the sheath into the left atrium 56. See FIG. 3B. When the catheter 14 is positioned in the left atrium 56, various procedures, such as mapping and ablation may be performed therein.

It will be noted that the location where the needle or other puncturing device passes through the interatrial septum 24 is of importance. Specifically, it is desirable that the device pass through the fossa ovalis. Found in the right atrium of the heart, the fossa ovalis is an embryonic remnant of the foramen ovale. In the fetal heart, the foramen ovale allows blood to enter the left atrium from the right atrium. It allows blood entering the right atrium to bypass the pulmonary circulation. In most individuals, the foramen ovale closes within the first year after birth to form the fossa ovalis. However, while being closed in most patients, the fossa ovalis remains considerably thinner than surrounding structure of the septum. Further, a puncture in the fossa ovalis will readily close in most patients.

Some experienced physicians are able to determine the location of the fossa ovalis in the interatrial septum by feel. That is, the physician determines location of the fossa ovalis based on his/her experience using a catheter 14 to probe the interatrial septum 24 and identify the location having the greatest compliance (e.g., the thinnest location). Such experience only comes with practice, and may be quickly lost if the physician does not perform the procedure on a regular basis. In any case, the number of doctors that can perform such a procedure is limited. Accordingly, the ability to measure the mechanical compliance of internal patient tissue such as myocardium may allow for improved catheter guidance as well as improved lesion formation.

Figure 4C:
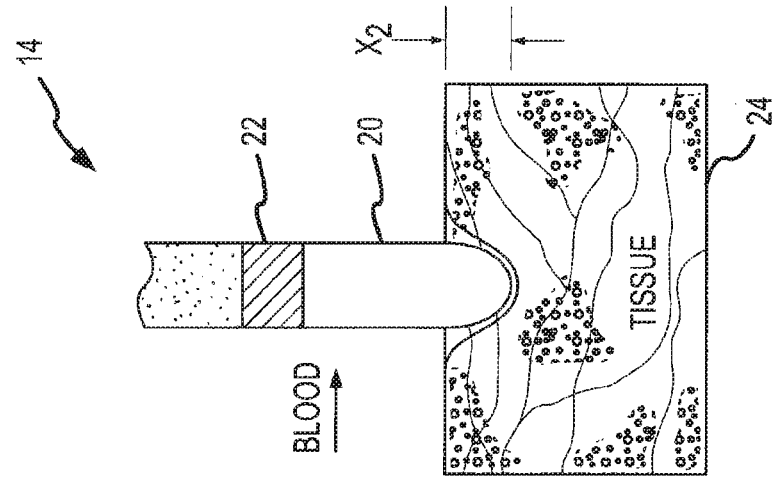
FIGS. 4A, 4B and 4C illustrate advancement of a catheter relative to internal patient tissue.
Figure 4B:
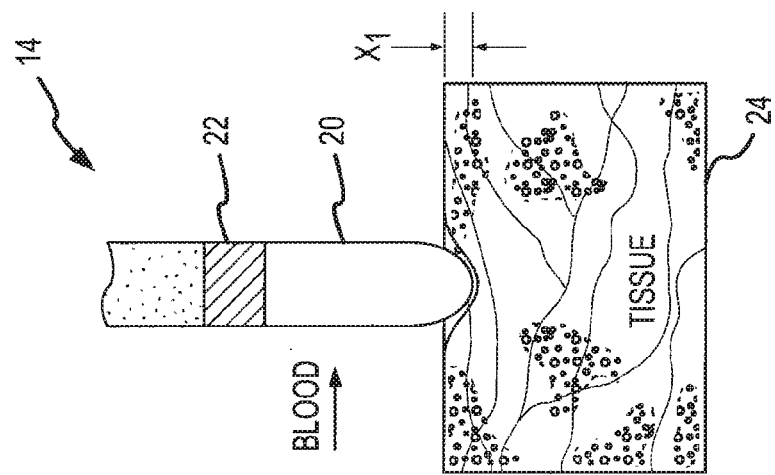
Figure 4A:
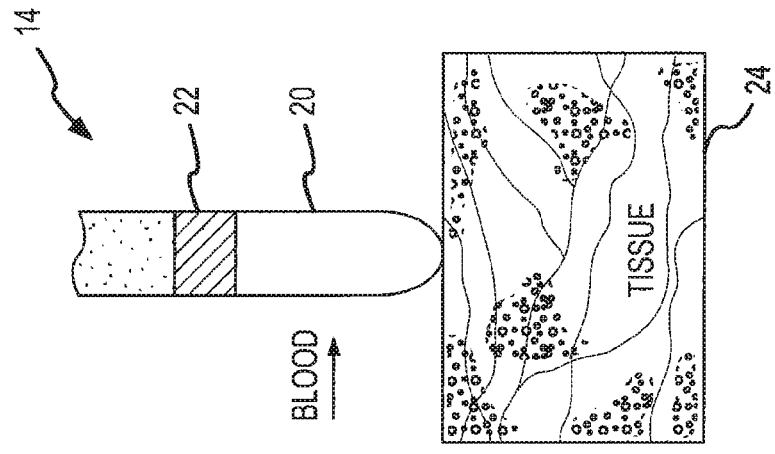

The mechanical compliance or elasticity of the myocardium or other internal tissue may be determined utilizing the catheter 14 incorporating the force transducer 22 as discussed above. Such elasticity may be determined by probing the patient tissue and measuring the force between a contact surface of the catheter (e.g., the tip electrode 20) and patient tissue and the displacement of the patient tissue. Such force and displacement measurements may be utilized to generate an elasticity value for a tissue location. As illustrated in FIG. 4A, the procedure begins by contacting the tip electrode 20 with the patient tissue. In this exemplary embodiment, the tissue is myocardial tissue of the interatrial septum 24. As will be appreciated, initial contact may be identified utilizing, for instance, impedance measurements. In this regard, the difference of resistivity between blood and myocardium tissue 24 causes an impedance change as the tip electrode 20 contacts the myocardium 24. This impedance change may be utilized to identify a position of initial contact, which may be utilized as a reference position.

Once initial contact is made, the electrode 20 may be displaced a first distance $x_1$ (e.g., relative to the reference position) to a first position. See FIG. 4B. At this time, the tissue 24 is compressed by the tip electrode 20. Generally, cardiac/myocardial tissue exhibits viscoelastic characteristics. In this regard, it shows a partial relaxation of force after a constant depth insertion is applied. However, the tissue also exhibits an elastic reaction force that provides a constant resistive force against the electrode 20 that remains after the tissue partially relaxes. Accordingly, the force transducer 22 may be utilized to measure this constant resistive force, for example, after the partial relaxation of the tissue. The resistive force $f_1$ and tissue displacement $x_1$ may be recorded. After this first measurement is made, the tip electrode 20 may be advanced to a second distance $x_2$ to a second position. See FIG. 4C. Again, the force transducer 22 may be utilized to measure the resistive force applied to the electrode tip 20 by the tissue. This second force $f_1$ and second tissue displacement $x_2$ may also be recorded. In this regard, two force measurements and two tissue displacement values are recorded for a single tissue location. It will be appreciated that additional incremental advancements of the tip electrode 20 and corresponding measurement by the force transducer 22 may be made. Of note, it may be desirable to obtain the different force measurements at a common point in the cardiac cycle. For instance, QRS or P wave gating may be implemented to assure that measurements are obtained at common cardiac cycle times.

The process of obtaining force and displacement measurements may be repeated at a plurality of different locations for a tissue area of interest. For instance, a plurality of probing measurements may be made on the interatrial septum. As will be discussed herein, such plurality of measurements may be utilized by a modeling system to identify elasticity of different areas of the septum.

Of note, it may be desirable to utilize the robotic actuator 60 to advance the catheter 14 and, hence, tip electrode 20 against the tissue 24. In this regard, it will be appreciated that such robotic actuation may provide for better movement control of the catheter as well as automated recording of tissue displacement. For instance, such robotic actuation may allow for sub-millimeter advancement. However, it will be appreciated that hand advancement may be utilized as well. For instance, markings may be provided on proximal portions of the sheath 8 and/or the shaft 6 of the catheter 14 that may provide an indication of displacement of the catheter to the sheath. Alternatively, a sensor may be utilized to monitor the position of the catheter relative to the distal end of the sheath. What is important is that a tissue displacement measurement is provided for each force measurement at each tissue location that is probed. Additional force and displacement measurements for each tissue location may increase the accuracy of a resulting elasticity determination.

As noted, cardiac/myocardial tissue exhibits at least partially elastic characteristics. Generally, the elastic characteristic of the tissue in response to a constant depth insertion follows a second order polynomial that approximates the relationship between the force and the penetration depth. Specifically:

$$F_{elastic} = K_1 x + K_2 x \qquad \text{Eq. (1)}$$

where F is the force as measured by the force transducer 22 and x is the penetration depth (i.e., tissue displacement). In this regard, the $K_1$ and $K_2$ values are representative of the elasticity of a probed tissue location. Such coefficients may be derived from two or more force and displacement measurements for a common tissue location. Accordingly, for each probe location, where at least two force and displacement measurements have been obtained, $K_1$ and $K_2$ may be obtained. In any case, upon determining $K_1$ and/or $K_2$, the probe location may be assigned an elasticity value. Such a value(s) may be applied to an output image/map generated by the system 10.

Further, stored data indicative of predetermined elasticity values may be utilized to generate an elasticity value for a force and/or displacement measurement. That is, a force measurement, a displacement measurement, or both may be utilized with, for example, predetermined look-up tables, equations, or other data (e.g., collectively catalog data) to determine an elasticity value for a tissue location. As will be appreciated, such stored data or catalog data may be determined clinically in animal and/or human trials/testing. In another arrangement, an operator (e.g., physician) may input data values into the system 10 (see FIG. 1). Force and/or displacement values may then be compared to the input data values. In this regard, the operator may input expected values associated with the elasticity, force and/or displacement for one or more internal regions (e.g., the fossa ovalis). That is, the measured values (force and/or displacement) may be compared to values set by an operator based on the experience of the operator.

Figure 5A:
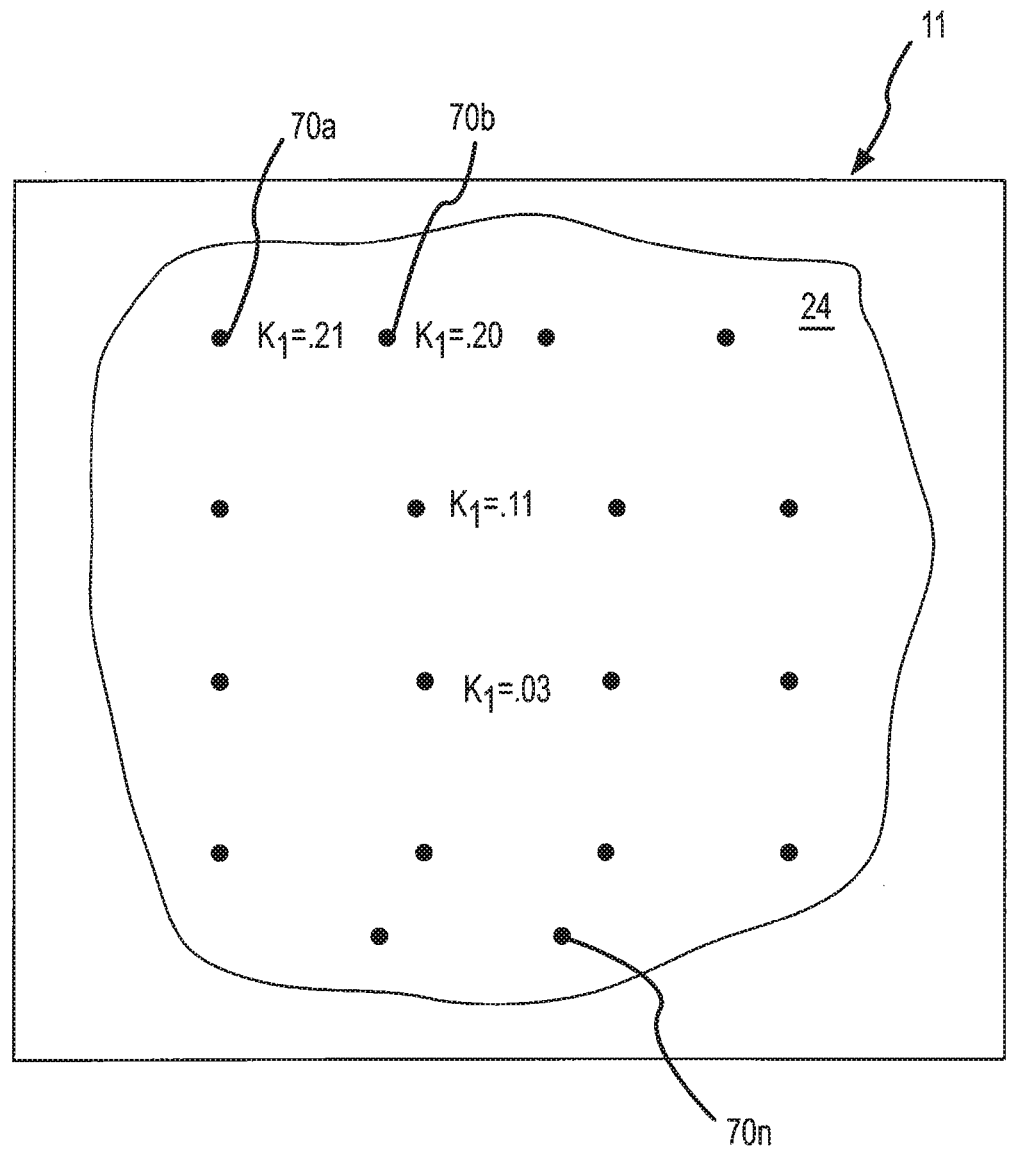
FIG. 5A illustrates a plurality of tissue contact locations and elasticity values as disposed on an image of an internal tissue area.

FIG. 5A illustrates an internal tissue area of interest as may be displayed on an output 11 of the system 10. In this exemplary embodiment, the area of interest is the interatrial septum 24. As a user probes the septum, an indication may be generated on the image indicating a tissue location that has been probed. As shown in FIG. 5A a plurality of tissue locations 70a-n within the tissue area may be probed an indication of each probed location may be correlated with the image. Further, a tissue elasticity value may be illustrated with each probed location. Upon generating an elasticity value for each probed tissue location 70, a graphical representation of the elasticity for the tissue area 24 may be generated. See FIG. 5B.

Figure 5B:
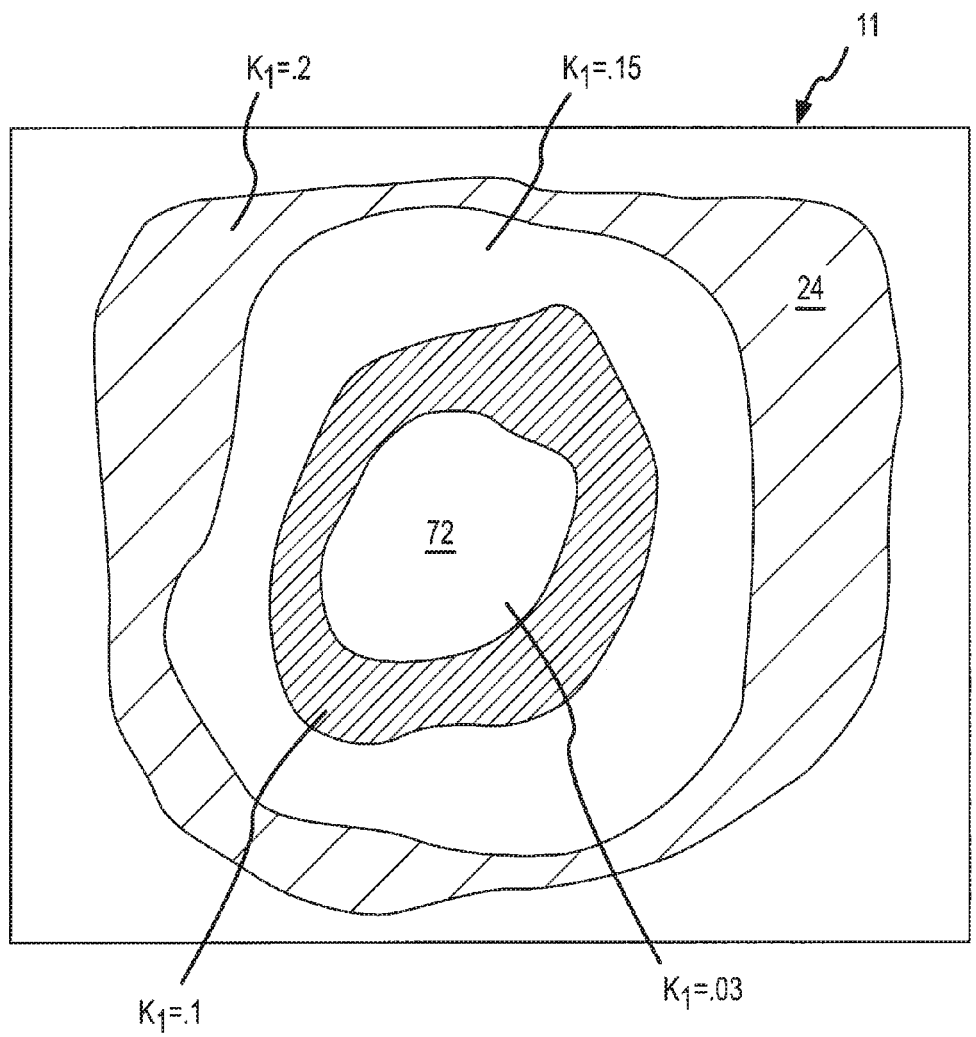
FIG. 5B illustrate a graphical representation of elasticity values as correlated with an image of an internal tissue area.

FIG. 5B illustrates modeling the elasticity values (e.g., $K_1$ and/or $K_2$) for different tissue locations 70 graphically. That is, the elasticity values may be surface modeled to provide, for example, a contour map representation of the elasticity for the probed tissue area 24. As shown, the region of lowest elasticity may correspond with the fossa ovalis 72, which is the thinnest structure within the interatrial septum 2 and has the lowest elasticity value $K_1$. That is, due to the thinness of this tissue, it provides little elastic resistance to displacement. In any case, tissue elasticities may be correlated with an image in order to provide a visual indication of different elasticity values for different tissue locations. Accordingly, a user may utilize this image to identify, for example, the fossa ovalis for performing a transseptal procedure. As will be appreciated, by providing such a graphical representation, a user (e.g., physician) may not rely entirely on their sense of feel to identify a transseptal access location in the interatrial septum.

Additionally, such information may be utilized for ablation purposes. As noted above, lesion size is determined in part by the force applied to the tissue. As will be appreciated, thinner areas of tissue may deflect more for a given displacement and therefore there may exist less force between an electrode and the tissue. Accordingly, the force between the electrode and the tissue may be adjusted in order to create a lesion with desired characteristics. In this regard, an elasticity map, such as shown in FIG. 5B, may also allow for adjustment of catheter-tissue contact force during an ablation procedure to provide desired lesion characteristics.

Furthermore, the elasticity values may be utilized to provide a warning to an operator. For instance, a warning (e.g., auditory and/or visual) may be issued to an operator based on the determination of the application of an excessive force in relation to a tissue elasticity value for a tissue location. Such an excessive force determination may be made, in one embodiment, by monitoring a ratio or a change in a ratio of elasticity (K) and force. Such warnings may be utilized to reduce the likelihood of unintended tissue puncturing.

Figure 6:
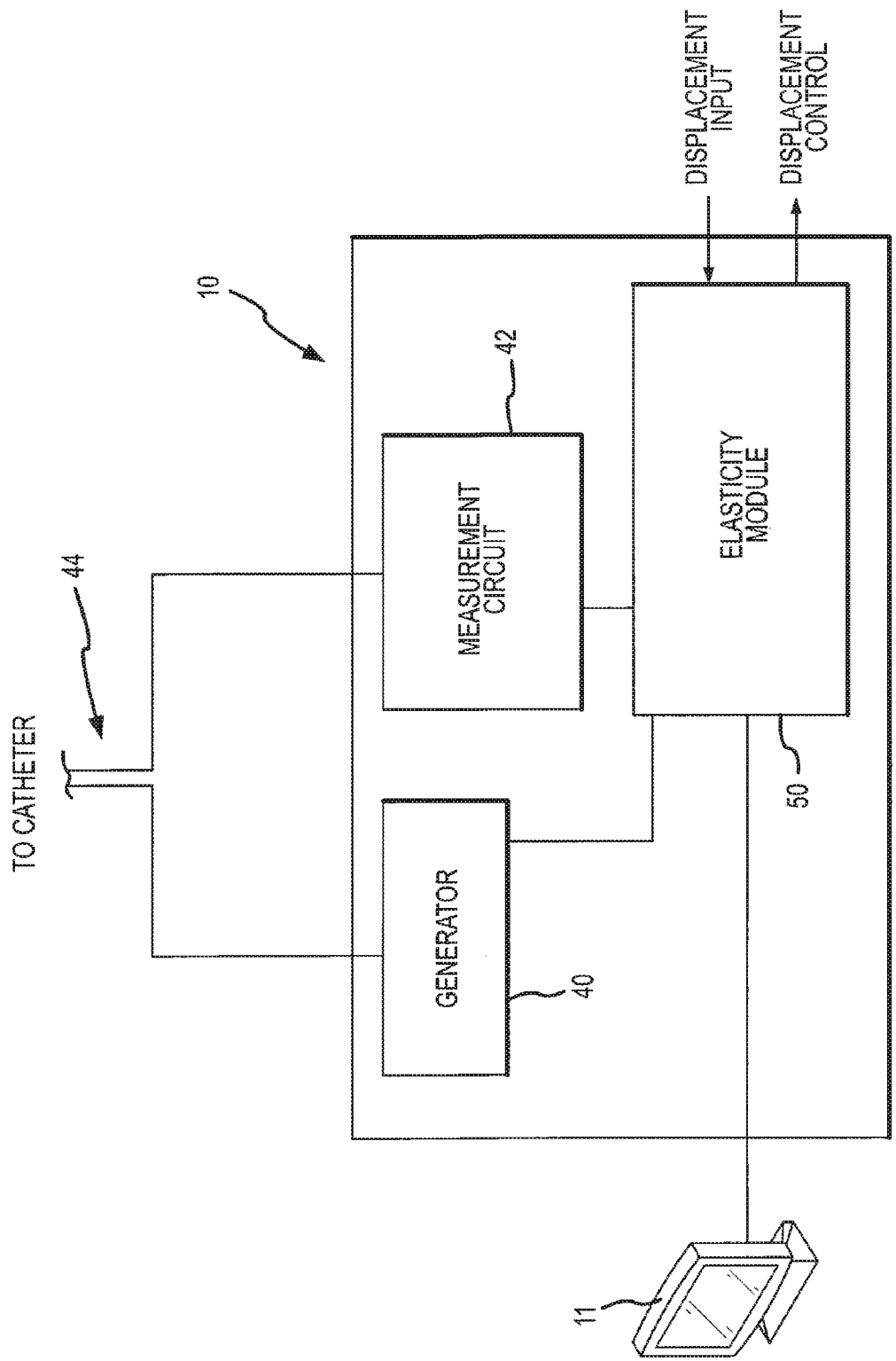
FIG. 6 illustrates a functional diagram of a system for determining tissue elasticity.

FIG. 6 is a functional block diagram showing the system 10 in more detail as it may be implemented to determine the elasticity of tissue contacted by the catheter 14. It is noted that some of the components typical of conventional tissue ablation and/or mapping systems are shown in simplified form and/or not shown at all in FIGS. 1 and 6 for purposes of brevity. Such components may nevertheless also be provided as part of, or for use with the catheter system 10. For example, electrode catheter 14 may include a handle portion, a fluoroscopy imaging device, and/or various other controls, to name only a few examples. Such components are well understood in the medical devices arts and therefore further discussion herein is not necessary for a complete understanding of the invention.

The exemplary system 10 may include a generator 40, such as, e.g., AC current generator and/or a radio frequency (RF) generator, which in the present embodiment provides an electrical signal(s) to the electrode(s) of the catheter 14 as well as to the force transducer 22 (as illustrated by wires 44). A measurement circuit 42 is electrically connected to the tip electrode 20 and force transducer 22. The measurement circuit 42 may measure any appropriate electrical responses associated with the electrodes and/or force transducer 22. The invention is not limited to use with any particular type or configuration of measurement circuit.

In an exemplary embodiment, the measurement circuit 42 may be operatively associated with an elasticity determination module 50 which may include a processor and memory. The module 50 is operative to analyze the response from the force transducer 22 and displacement information to determine an elasticity value. In relation to the displacement information, such information may be provided by a robotic actuator or a position sensor associated with the catheter. Alternatively, such information may be input by a user. The module 50 may also generate displacement control signals to control the displacement of the catheter (e.g., by a robotic actuator) for force measurement purposes.

The module 50 may utilize sets of force and displacement values to determine the elasticity values for probed tissue locations. Such elasticity values may alternatively be stored in memory, e.g., as tables or other suitable data structures. The module 50 may then access the tables or equations in memory and determine an elasticity value a probed tissue location based on force and displacement information. The module may also correlate the elasticity value and location with an image provided on user output display 11.

Figure 7:
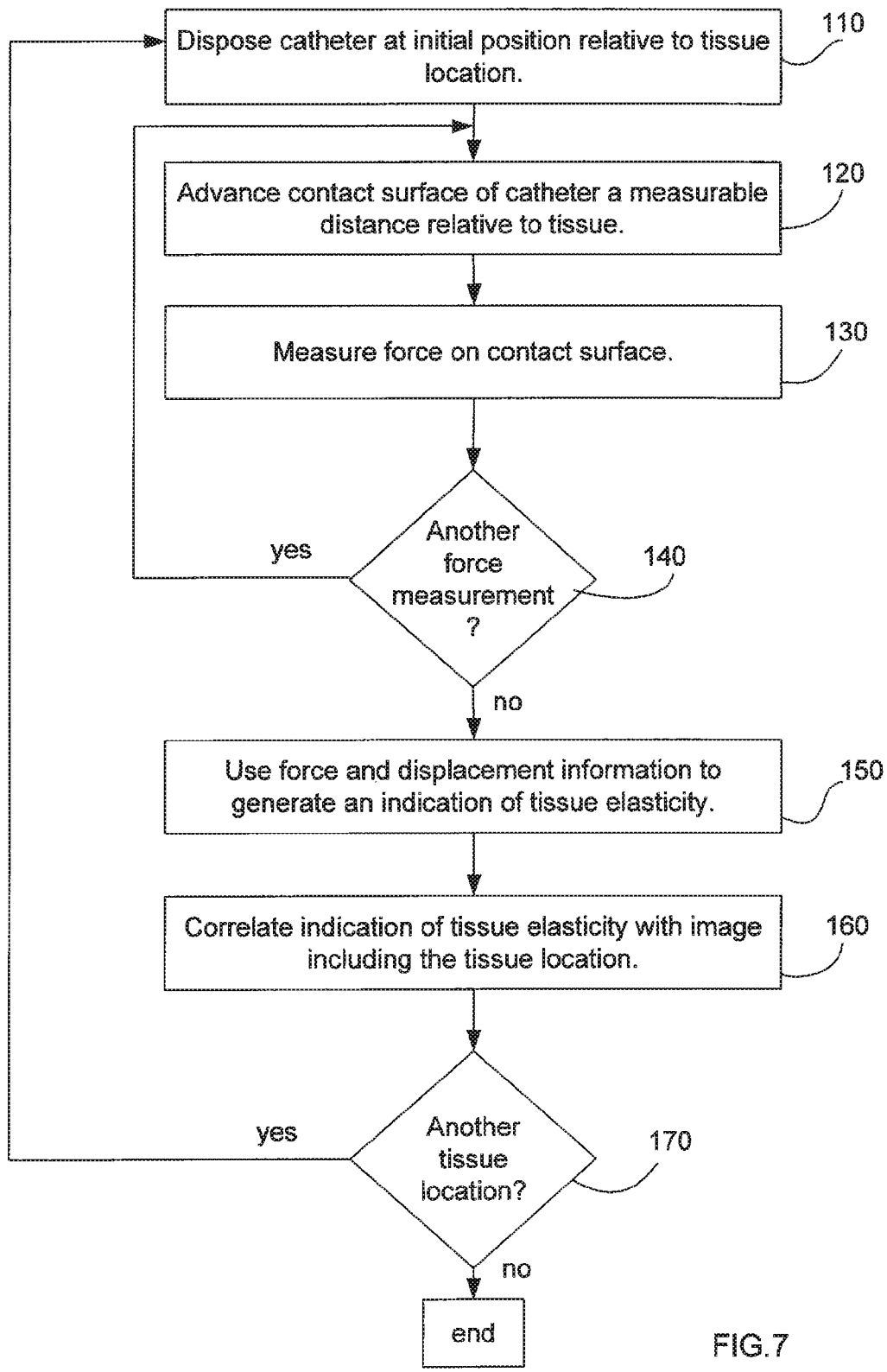
FIG. 7 illustrates a protocol for use in determining internal tissue elasticity.

FIG. 7 illustrates a protocol 100 that may be utilized to determine elasticity values for internal patient tissue. Initially, a contact surface of a catheter is disposed (110) at an initial position relative to a first location of an internal patient tissue area. Typically, such an initial position is a contact position where the tissue is not compressed or deflected. However, the initial contact position may include an initial compression. Once disposed (110) at the initial position, the contact surface is advanced (120) a predetermined distance to a first measurement position relative to the tissue. At this measurement position, the tissue is compressed or deflected and thereby applies a resistive force to the contact surface. At a predetermined time after advancement, a force measurement is obtained (130). If another of force measurement is desired, the contact surface is again advanced (120) a predetermined distance to another measurement position relative to the tissue. Likewise, another force measurement is obtained (130) this process may be repeated until a predetermined number of force measurements for a corresponding displacements are obtained. The acquired data, including the force measurements and tissue displacement values associated advancement of the contact surface, are utilized to generate (140) an indication of tissue elasticity. Once such an indication is generated, the indication of elasticity for the first tissue location may be correlated (150) with an image that may be output to a user. If elasticity information for additional tissue locations is desired, the process may be repeated for additional locations.

Although various embodiments of this invention have been described above with a certain degree of particularity, those skilled in the art could make numerous alterations to the disclosed embodiments without departing from the spirit or scope of this invention. For example, different arrangements exist for determining the force between a contact surface of a catheter and patient tissue. Further, additional arrangements exist for determining the displacement of the catheter and/or patient tissue. An important feature of this invention is the correlation of the force and displacement to generate an indication of tissue elasticity and use of this information for performing a medical procedure. Further it will be appreciated that all directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method for performing a medical procedure, the method comprising:
   receiving a signal from a catheter contacting at least a first tissue location of an internal tissue area;
   processing said signal to generate a tissue elasticity value for at least the first tissue location;
   altering an image of the internal tissue area displayed on a display device to provide a visual representation of said tissue elasticity value at the first tissue location; and
   upon at least one tissue elasticity value exceeding a predetermined threshold, generating a warning output indicating an excessive applied force in relation to said at least one tissue elasticity value.

2. The method of claim 1, wherein generating the warning output comprises at least one of:
   generating an audio warning output; and
   generating a visual warning output via the display device.

3. The method of claim 1, further comprising:
   receiving a plurality of signals from the catheter corresponding to the catheter contacting a plurality of tissue locations;
   processing said plurality of signals to generate tissue elasticity values for each of the plurality of tissue locations; and
   altering said image on the display device to provide a visual representation of said tissue elasticity values at each of the plurality of tissue locations.

4. The method of claim 1, wherein altering said image comprises altering a topographical map of the internal tissue area.

5. The method of claim 1, wherein altering said image comprises providing a color gradient on said image to provide said visual representation.

6. The method of claim 1, wherein generating an image comprises generating a three-dimensional model of the internal tissue area.

7. The method of claim 1, further comprising:
   generating a visual indication on the display device of a tissue structure of interest.

8. The method of claim 7, wherein generating a visual indication of a tissue structure of interest comprises generating a visual indication of a fossa ovalis area of an interatrial septum on the display device.

9. The method of claim 1, wherein generating said tissue elasticity value comprises:
   receiving an impedance measurement of an electrode of the catheter that contacts tissue of said internal tissue area; and
   processing said impedance measurement to generate said tissue elasticity value.

10. An apparatus for use in a medical procedure, comprising:
    an input operative to receive a signal indicative of a level of force between a catheter and at least a first tissue location of an internal tissue area;
    a tissue elasticity assessment module operative to process said signal to determine a tissue elasticity value of the first tissue location and to monitor for excessive force between the catheter and the first tissue location; and
    an output operative to:

provide said tissue elasticity value for use in presenting a first visual indication of said tissue elasticity value of the first tissue location on an image of the internal tissue area; and provide a warning output upon said tissue elasticity value exceeding a predetermined threshold for use in issuing a warning indicating an excessive applied force in relation to said tissue elasticity value.

11. The apparatus as set forth in claim 10, further comprising a first data structure; wherein said first data structure comprises at least one tissue elasticity value related to at least one force value.

12. The apparatus as set forth in claim 10, wherein said tissue elasticity assessment module is operative to determine a plurality of tissue elasticity values for a plurality of tissue locations.

13. The apparatus as set forth in claim 12, wherein said output is operative to provide said plurality of tissue elasticity values to an imaging system, wherein the imaging system is operative to provide a plurality of visual indications of said plurality tissue elasticity values of the plurality of tissue locations on the image of the internal tissue area.

14. The apparatus as set forth in claim 10, wherein said tissue elasticity assessment module is operative to generate actuator control signals and wherein said output provides said actuator control signals to a robotic actuator, wherein the robotic actuator is operative to controllably displace the catheter in accordance with said actuator control signals.

15. The apparatus as set forth in claim 10, wherein said tissue elasticity assessment module is operative to generate signal generator control signals and wherein said output provides said signal generator control signals to a signal generator adapted to provide power to an ablation electrode of the catheter, wherein a level of the power is selected based at least in part on said elasticity value.

16. The apparatus as set forth in claim 10, wherein said tissue elasticity assessment module is operative to receive first and second signals indicative of first and second levels of force between the catheter and the first tissue location.

17. The apparatus as set forth in claim 16, wherein said tissue elasticity assessment module is operative to receive first and second displacement values associated with displacements of said catheter relative to said first tissue location.

18. The apparatus as set forth in claim 10, wherein said tissue elasticity assessment module is operative to process an impedance measurement received from said input to determine the tissue elasticity value of the first tissue location.

19. A medical system comprising:
an input operative to receive a signal from an ablation electrode of a catheter configured for disposition at an internal tissue location, wherein the ablation electrode forms a contact surface on a distal end of the catheter;
a measurement device operative to measure an impedance value of said signal wherein said impedance value is indicative of a force between said contact surface and a first internal tissue location contacted by the contact surface;
a tissue elasticity assessment module operative to generate an indication of elasticity, based on said impedance value, for the first tissue location contacted by said contact surface; and
a signal generator adapted to provide power to the ablation electrode wherein a level of said power is selected based at least in part on said indication of elasticity.

20. The system of claim 19, further comprising:
an imaging system operative to generate an image of the internal tissue location on a display device, wherein said imaging system is operative to receive said indication of elasticity from said tissue elasticity assessment module and to generate a first visual indication of said tissue elasticity value at the first internal tissue location.

21. The system of claim 20, wherein said tissue elasticity assessment module is further operative to provide a warning output upon said indication of tissue elasticity exceeding a predetermined threshold.

22. The system of claim 19, further comprising a first data structure, wherein said first data structure comprises at least one tissue elasticity value related to at least one impedance value.

23. The system of claim 19, further comprising:
a robotic actuator, operatively interconnected to said tissue assessment module, wherein said robotic actuator is operative to controllably move the catheter.

24. A medical system comprising:
an input operative to receive a signal from an electrode of a catheter configured for disposition at an internal tissue location, wherein the electrode forms a contact surface on a distal end of the catheter;
a measurement device operative to measure an impedance value of said signal wherein said impedance value is indicative of a force between said contact surface and a first internal tissue location contacted by the contact surface;
a tissue elasticity assessment module operative to generate an indication of elasticity, based on said impedance value, for the first tissue location contacted by said contact surface, wherein said tissue elasticity assessment module is further operative to provide a warning output upon said indication of tissue elasticity exceeding a predetermined threshold.

25. The system of claim 24, further comprising:
an imaging system operative to generate an image of the internal tissue location on a display device, wherein said imaging system is operative to receive said indication of elasticity from said tissue elasticity assessment module and to generate a first visual indication of said tissue elasticity value at the first internal tissue location.

* * * * *